(12) United States Patent
Peffley et al.

(10) Patent No.: US 6,583,335 B1
(45) Date of Patent: Jun. 24, 2003

(54) DIRECT TRANSFORMATION OF HIGHER PLANTS THROUGH POLLEN TUBE PATHWAY

(75) Inventors: Ellen B. Peffley; Randy Allen; Ping Song, all of Lubbock; Xiaomin Shang, Plano, all of TX (US)

(73) Assignee: Texas Tech University, Lubbock, TX (US)

( * ) Notice: Subject to any disclaimer, the term of this patent is extended or adjusted under 35 U.S.C. 154(b) by 0 days.

(21) Appl. No.: 08/844,023

(22) Filed: Apr. 18, 1997

(51) Int. Cl.[7] .................... C12N 15/82; C12N 15/87; A01H 1/02; A01H 5/00
(52) U.S. Cl. .................... 800/278; 800/260; 435/430; 435/430.1; 435/431; 435/468
(58) Field of Search .................... 435/172.3, 252.2, 435/410, 468, 469, 470, 478, 430, 430.1, 431; 800/205, DIG. 56, 290, 294, 278, 260

(56) References Cited

U.S. PATENT DOCUMENTS

| | | | |
|---|---|---|---|
| 4,827,079 A | 5/1989 | Evans et al. ................ | 800/1 |
| 4,897,345 A | 1/1990 | Harris et al. ................ | 435/7 |
| 4,940,839 A | 7/1990 | Bravo et al. ................ | 800/220 |
| 5,066,594 A | 11/1991 | DeBonte et al. .......... | 435/240.4 |
| 5,066,830 A | 11/1991 | Morrison et al. .......... | 435/172.3 |
| 5,086,169 A | 2/1992 | Mascarenhas .............. | 536/27 |
| 5,175,095 A | 12/1992 | Martineau et al. ......... | 435/69.1 |
| 5,367,111 A | 11/1994 | Ohsumi et al. ............. | 800/200 |
| 5,405,765 A | 4/1995 | Vasil et al. ................. | 435/172.3 |
| 5,428,146 A | 6/1995 | Logemann et al. ......... | 536/24.1 |
| 5,530,185 A | 6/1996 | Martineau et al. ......... | 800/205 |
| 5,549,729 A | 8/1996 | Yamashita .................. | 71/26 |
| 5,552,139 A | 9/1996 | Shoseyov et al. .......... | 424/944 |
| 5,567,599 A | 10/1996 | Lemieux .................... | 435/172.3 |

OTHER PUBLICATIONS

Potrykus. Ann. Rev. Plant. Physiol. 1991. vol. 42: 205–225.*
Takagi et al. Kagawa Daigaku Nogakubu Gakujutsu Hokoku. 1992. vol. 44:11–17. Abstract.*
Kenzelmann and Muhlemann. Biotechniques. 1997. vol. 23:204–206.*
Luo et al., "A Simple Method for the Transformation of Rice Via the Pollen–Tube Pathway," *Plant Molecular Biology Reporter* 6(3):165–74 (1988).
"Gene Transfer to Plants: Assessment of Published Approaches and Results," *Ann. Rev. Plant Physiol. Plant Mol. Biol.* 42:205–25 (1991).
C.C. Eady, "Towards the Transformation of Onion (*Allium cepa*)." *New England Journal of Crop and Horticultural Science* 23:239–50 (1995).
Hahne et al., "Dimethyl Sulfoxide Can Initiate Cell Divisions of Arrested Callus Protoplasts by Promoting Cortical Microtubule assembly," *Proc. Natl. Acad. Sci. USA* 81:5449–54.
De Block et al., "Transformation of *Brassica napus* and *Brassica oleracea* Using *Agrobacterium tumefaciens* and the Expression of the bar and neo Genes in the Transgenic Plants," *Plant Physiol.* 91:694–701 (1989).
Matzke et al., "How and Why Do Plants Inactivate Homologous (Trans)genes?," *Plant Physiol.*

\* cited by examiner

*Primary Examiner*—David T. Fox
(74) *Attorney, Agent, or Firm*—Nixon Peabody LLP (57) ABSTRACT

A genetic transformation system via the pollen tube pathway is presented, plasmid DNA prepared with each of 4 different methods was applied to the surface of an ovary wound site after removal of the style of florets following pollination. Movement of the plasmid DNA indicated plasmid DNA reached the ovules of decapitated florets within about 24 hours after its application to the surface of remaining styles or ovary wound site after pollination. Based on the result of PCR analyses of genomic DNA, 12% to 15% of the plants tested had the 282 bp fragment, the specific portion of the luciferase gene construct into the genome. Southern blotting of genomic DNA from PCR positive plants indicated that the firefly luciferase gene construct may have been incorporated into the genomic DNA of the plants. Some of the PCR positive plants, derived from seeds harvested from florets treated with a DNA solution preparation, still had the 282 bp fragment of the luciferase gene construct in their sexually produced progenies, indicating that transformation via the pollen tube pathway has the potential to produce stably transformed plants.

19 Claims, 3 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer
      sequence

<400> SEQUENCE: 1
ggatatgggc tcactgagac                                                    20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer
      sequence

<400> SEQUENCE: 2
gaagtgttcg tcttggtccc ag                                                 22

<210> SEQ ID NO 3
<211> LENGTH: 308
<212> TYPE: DNA
<213> ORGANISM: Allium cepa

<400> SEQUENCE: 3
gctcggtacc cggatatggg ctccatgaga ctacatcagc tattctgatt a cacccgagg       60 gggatgataa accgggcgcg gtcggtaaag ttgttccatt ttttgaagcg a aggttgtgg      120 atctggatac cggaaaacg ctgggcgtta atcagtgagg cgaataatgt g tcagaggac      180 ctatgattat gtccggttat gtaaacaatc cggaagcgac caacgccttg a ttgacaagg      240 atggatggct acatcattca ggagacatag cttactggga cgaagacgaa c acttcgggg      300 atcctcta                                                                308

<210> SEQ ID NO 4
<211> LENGTH: 285
<212> TYPE: DNA
<213> ORGANISM: Photinus pyralis

<400> SEQUENCE: 4
ggatatgggc tccatgagac tacatcagct attctgatta cacccgaggg g gatgataaa      60 ccgggcgcgg tcggtaaagt tgttccattt tttgaagcga aggttgtgga t ctggatacc     120 gggaaaacgc tgggcgttaa tcagtgaggc gaataatgtg tcagaggacc t atgattatg     180 tccggttatg taaacaatcc ggaagcgacc aacgccttga ttgacaagga t ggatggcta     240 catcattcag gagacatagc ttactgggac gaagacgaac acttc                      285

DIRECT TRANSFORMATION OF HIGHER PLANTS THROUGH POLLEN TUBE PATHWAY

FIELD OF THE INVENTION

This invention relates to transformation of plants via the pollen tube pathway through applications of DNA solutions directly to the surface remaining after styles of florets are removed following pollination. In another aspect, the direct transformation of plants is achieved by applying solutions containing donor DNA directly to a wound site on the ovary following removal of styles which has been previously pollinated with mentor pollen while allowing for the formation of pollen tubes extending from the style into the ovule.

BACKGROUND OF THE INVENTION

Plant transformation has been achieved through various means. The first to be developed and most frequently used employs *Agrobacterium tumefaciens* as a vector to introduce alien DNA into the genome of the targeted plant. This technique was initially limited to the host plants of *A. tumefaciens* (i.e. dicotyledons), but was recently successfully applied to a monocot, corn, *Zea mays* L., [Gould et al, *Plant Physiol.*, 95, 426–434 (1991)]. However, success of the technique remains dependent upon the ability to regenerate plants from infected explants. For most important crops, this ability has not been developed or is not compatible with the needs of the transformation technique through *A. tumefaciens*.

Other currently known techniques for transformation, include electroporation and bombardment with DNA-coated microprojectiles. In the case of electroporation, the technique has only been successful for species that can be regenerated from protoplasts.

Microprojectile bombardment to introduce alien DNA into the genome of a host plant is exemplified. In soybean, *Glycine max* L., bombardment of over 20,000 shoot-apices only resulted in transient expression of the transforming gene whereas bombardment of embryogenic suspensions with the same gene produced several transformed plants.

Current techniques of plant transformation, i.e. electroporation and microprojectile bombardment require the ability to regenerate plants from single cells. For most crops, this ability has yet to be developed despite repeated efforts. These techniques also require sophisticated technical skills and facilities.

Accordingly, there is a need for a technique of direct plant transformation with fewer requirements that will be applicable to most crops, easy to implement and cost effective. There is a need for a technique of direct transformation that eliminates the need to regenerate plants from cultured explants.

The delivery of foreign DNA into plants via pollen tube pathway has been reported. In earlier work, the total genomic DNA from a donor plant were injected into the axial placenta of recipient plants about a day after self-pollination. The genomic DNA was partially protected from shearing and hydrolysis by partially recombination of the DNA with histones. It was found that foreign DNA could transform the embryo by entering the ovule, following the path along with the pollen tube grew, and a great number of mutant offsprings were obtained. However, no molecular evidence was presented to confirm that the phenotypic changes seen in the mutant offsprings of recipient plants were caused by the exogenous DNA from the donor plants.

SUMMARY OF THE INVENTION

The present invention relates to a method for transformation of plants by direct application of exogenous DNA solution into a wound site on the ovary after removal of styles which have been previously pollinated with mentor pollen, allowing for the formation of pollen tubes extending from the style into the ovule. Preferably, the exogenous DNA sequence will correspond to a desired physical or functional characteristic to be imparted to the host plant. The DNA sequence is introduced into the host plant genome, thus producing a transformed plant embryo.

Current methods of transformation generally require passage through a tissue culture cycle, thus, only plants amenable to culture (i.e. regeneration capability) are used as recipients. Few culture systems have been worked out; however, the present inventive method is attractive for the transformation of many different plants because there is no need for tissue culture. The present methodology does not require the bombardment of tissues, and unlike these prior taught systems, does not require expensive equipment and personnel trained in the art of tissue culture. The present method is relatively simple and it can be used to introduce multiple gene constructs in a single application, unlike other systems. The results achievable are like a backcross method of breeding plants. The direct introduction of DNA without markers would be more stably incorporated into genomes.

Even though the direct transformation of higher plants through pollen tube pathway is suitable for a variety of flowering plants, the present disclosure is focused on the onion plant. Onion is an important monocotyledonous vegetable grown on all the continents of the world. The common bulb-type onion, *Allium cepa* L., are by far the most important onions in commercial trade. Depending on its adaptation, it can bulb under either long-or short-day conditions. It produces a single bulb and has an umbel type inflorescence that produces true seeds. Bulbing is controlled by a combination of day length and temperature. Several closely related species include *A. cepa*, including the edible species *A. fistulosum* L. (Japanese bunching or Welsh onion), *A. satiuum* L. (garlic), *A. ampeloprasum* L. (great-headed garlic, leek, and Kurrat), *A. chinene Maxim* (rakkyo), *A. schoenoprasum* L. (chives) and *A. tuberosum* L. (Chinese chives). Onion has become an essential part of man's diet mainly for its flavoring qualities. There seems to be no limit to its use by any nationality.

In the United States, onions are produced in many regions as one of the major vegetables. In 1992, it ranked third in both acreage and value among the eleven principal commercial vegetables with a total of 147,200 acres and $613,620,000. In Texas, onion was the number one vegetable crop with 19,500 acres of production and had a value of $61,022,000 in 1992 (USDA, Vegetables Annual Summary, 1992).

Onion has been greatly improved in characteristics such as quality, yield, and uniformity by classic plant breeding methodology. Development of onion cultivars resistant to fungal, bacterial, and viral diseases has been a major project by public and private breeders for many years. However, genetic variability for disease resistance within accessions of *A. cepa* is limited, but resistance to some of the diseases has developed within locally adapted *A. cepa* forms. Some related species (*A. fistulosum, A. galanthum, A. royelii*) could contribute germplasm for resistances in breeding programs. Unfortunately, resistance from these related species have not successfully been introduced into commercial *A. cepa* cultivars because of post-fertilization barriers such as hybrid embryo abortions during early embryo development in interspecific hybridization in the genus Allium. Ovule culture was not sufficient to overcome post-fertilization barriers restraining normal hybrid plant development (Bino et al., 1989; Gonzalez & Ford-Loyd, 1987). Besides a high degree of hybrid sterility, limited genetic recombination between the different genomes of Allium also limits the use of interspecific hybridization for onion improvement (Novak et al., 1986). One of the ways to bypass the pre- or post-fertilization barriers in interspecific hybridization is genetic transformation.

Genetic transformation transcends classical plant breeding by permitting the rapid transfer of genetic traits between entirely different organisms. Potential benefits include enhanced nutritional value from crops by changing amino acid composition or increasing protein content, reductions in pesticide usage, and herbicide usage by transferring insect, disease and herbicide resistant genes into cultivars. Genetic transformation technologies such as Agrobacterium-mediated and microprojectile bombardment-mediated transformation techniques have really been developed to supplement conventional plant breeding techniques. The introduction and expression of foreign DNA have been used to modify basic aspects of physiology and development and to introduce commercially important characteristics such as herbicide and insect resistance into plants. Agrobacterium-based transformation systems have been widely used in dicotyledonous plant species. Most monocotyledonous plants are insensitive to Agrobacterium infection, and subsequent transformation are not successful. Several techniques for direct DNA delivery into cells including chemical mediated uptake of DNA into isolated protoplasts, electroporation, injection, and the use of high-velocity particles to introduce foreign DNA into intact tissue. However, all of these transformation techniques involve plant cell and tissue culture and subsequent plant regeneration, which sometimes is not easy to achieve because of genotype dependence.

In accordance with the present invention, a direct method for the delivery of foreign DNA into plants is the pollen tube pathway. This method involves applying foreign DNA onto the excised style of a recipient plant after pollination. Although the pollen tube pathway is not widely accepted because molecular evidence to confirm the genetic transformation by this method is limited, this technique has significant potential as a plant genetic transformation system. It has the following advantages over Agrobacterium-mediated or other direct gene delivery systems: (1) elimination of cell or tissue culture and regeneration systems; (2) low cost; (3) genotype independence; (4) avoidance of somaclonal variation; and (5) higher transformation efficiency.

The objective of this research was to (1) optimize the timing of exogenous DNA application after pollination, which was crucial for the transformation of meristematic cells that give rise to reproductive structures; (2) investigate the effect of different components in exogenous DNA solution on the delivery of foreign DNA; and (3) recover whole transgenic onion plants via pollen tube pathway.

DETAILED DESCRIPTION OF THE INVENTION

The present invention is directed to a method for producing transformed plants inclusive of all flowering plants. As described herein, the present invention provides for the direct transfer of exogenous DNA to host plants and integration of the exogenous DNA into the host plant genome. Progenies of the transgenic plants inherit the extra chromosomal DNA.

As used herein, the term "exogenous DNA", or "foreign DNA" refers to DNA originating from a source outside the host or recipient plant. The term "DNA segment" refers to a DNA sequence having the nucleotide based composition and length capable of being introduced into the genome or a gene complex of a host plant. The term "host plant" refers to a plant chosen to receive an exogenous DNA segment. The term "gene" refers to a segment of DNA composed of a transcribed region and a regulatory sequence that makes transcription possible and can, either alone or in combination with other genes, provide the organism with an identifiable trait.

The term "trait" refers to detectable physical or functional characteristic of an organism. The term "phenotype" is a particular manifestation of a trait which corresponds to the presence of a particular gene. The term "homology" refers to two regions of DNA which contain regions of nearly identical DNA sequences. "Transformant" refers to a host plant which has been transformed with genetic material according to the methodology of the invention. Similarly, "transgenic" is used herein to include any plant, plantlet, or fertilized ovule the genotype of which has been altered by the presence of "heterologous, exogenous, or foreign DNA", wherein the DNA was introduced into the genome by the described genetic engineering process according to the invention, or which was initially introduced into the genome of a parent plant by the process of the present invention and is subsequently transferred to later generations by sexual crosses or asexual propagation.

As used herein "genome" refers to the sum total of hereditary genetic material within a cell's chromosomes. The term "heritable" means that the DNA is capable of transmission through at least one complete sexual cycle of a plant, i.e., it is passed from one plant through its gametes to its progeny plants. As used herein, the term "plasmid" refers to autonomously replicating extrachromosomal DNA which is not integrated into a microorganism's genome and is usually circular in nature.

In addition, abbreviations are utilized in further describing the present invention as follows:

| LIST OF ABBREVIATIONS | |
|---|---|
| EDTA | Ethylenediaminetetraacetic acid |
| SDS | Sodium dodecylsulfate |
| PCI | Phenol/Chloroform/Isopropanol |
| CI | Chloroform/Isopropanol |
| MS | Murashige & Skoog Medium (1964) |
| NAA | Naphthalene acetic acid |
| $GA_3$ | Gibberrellic acid |
| PEG | Polyethylene glycol |
| DMSO | Dimethyl sulfoxide |
| CTAB | Hexadecyl tri-methylammonium bromide |
| PCR | Polymerase Chain Reaction |
| x-gal | Bromo-4-chloro-3-indolyl-b-galactoside |
| IPTG | Isopropylthio-b-D-glactoside |
| GUS | B-1, 3-Glucuronidase |
| DAPI | 4'6-diamidino-2-phenylindole |
| PI | Propidium iodide |
| DAA | Days after anthesis |
| EB | ethidium bromide |
| HEPES | N-2-hydroxyethylpiperazine-N-2-ethanesulfonic acid |
| DEPC | Diethyl pyrocarbonate |
| BSA | Bovine Serum Albumin |

Figure 1:
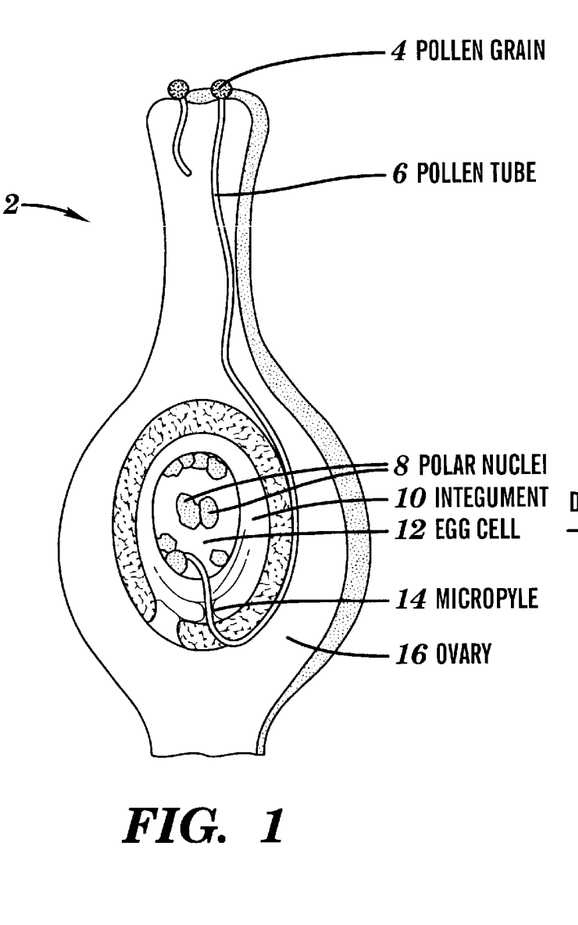
FIG. 1 is a cross-sectional side view of a plant ovary inclusive of the pollen tube and other elements of the fertilized system.
Figure 2:
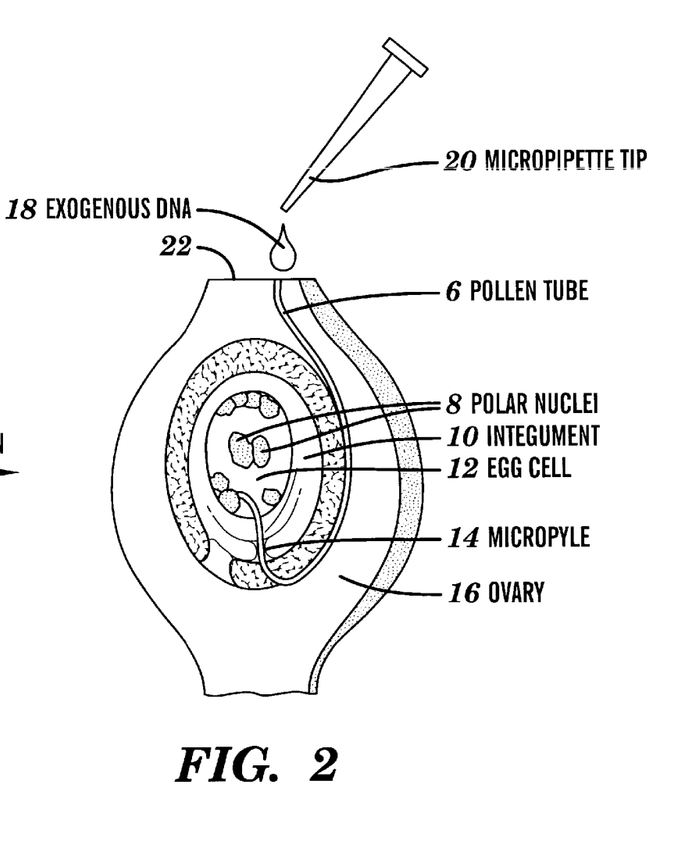
FIG. 2 is a cross-sectional side view of the same ovary, pollen tube with the pollen tube having been removed leaving a wound site for direct introduction of exogenous DNA.

The cross-sectional side view presented in FIG. 1 of a plant female reproduction system 2 comprised of the various production system elements including pollen grain 4, pollen tube 6 and ovary 16. The ovary 16 is shown with polar nuclei 8 and integument 10 along with egg cell 12 and micropyle 14. The cross-sectional side view of the same onion reproduction system 2 of FIG. 1 is shown in FIG. 2 wherein a droplet of exogenous DNA 18 is being introduced to an opening of the pollen tube 6 along an ovary wound site 22 from a micropipette tip 20.

Figure 3:
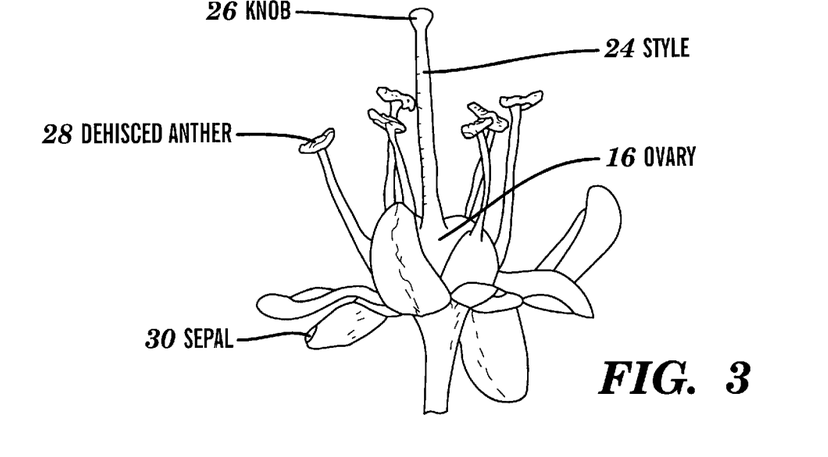
FIG. 3 is a side view of an onion floret.
Figure 4:
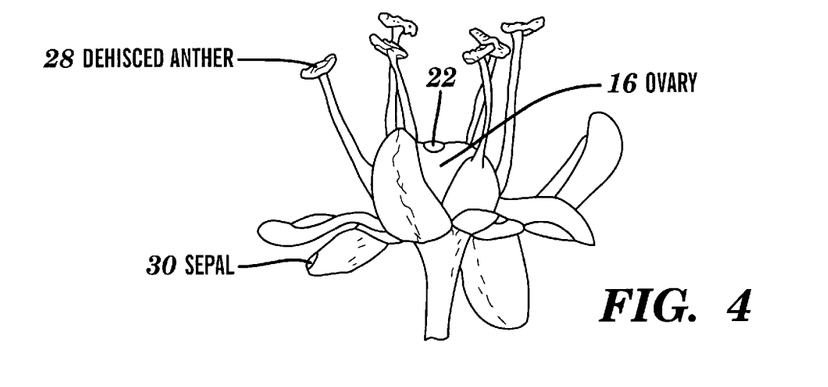
FIG. 4 is a side view of the onion floret of FIG. 3 with the style removed, leaving a wound site on the ovary.
Figure 5:
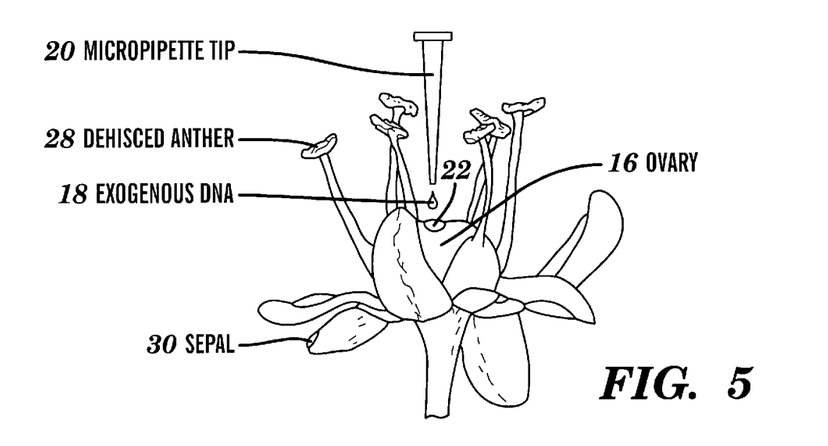
FIG. 5 is the view of FIG. 4 showing micropipette delivery of a solution of exogenous DNA to the ovary wound site.

FIGS. 3, 4 and 5 present a side view of an onion floret. In FIG. 3 the onion floret style 24 and a stigmatic knob 26 are positioned on ovary 16. Dehisced anther 28 are shown along with perianth 30 representing an untouched or modified onion floret. In FIG. 4, the same onion floret shown with the style 24 removed leaving a wound site 22 on the ovary. FIG. 5 is a view of FIG. 4 showing a micropipette 20 in position for delivering a direct application of exogenous DNA solution 18 to the wound site 22 on the ovary 16.

Figure 6:
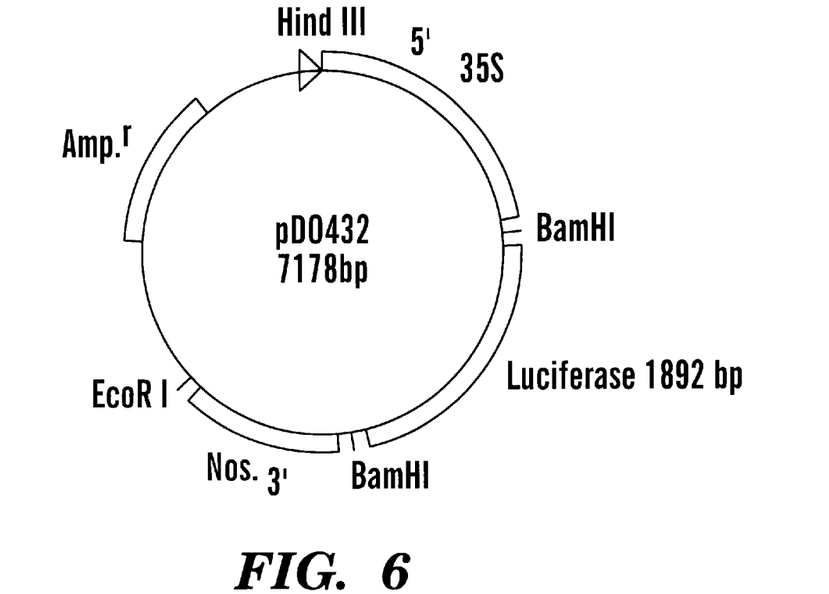
FIG. 6 is a construct map of plasmid pDO432.
Figure 7:
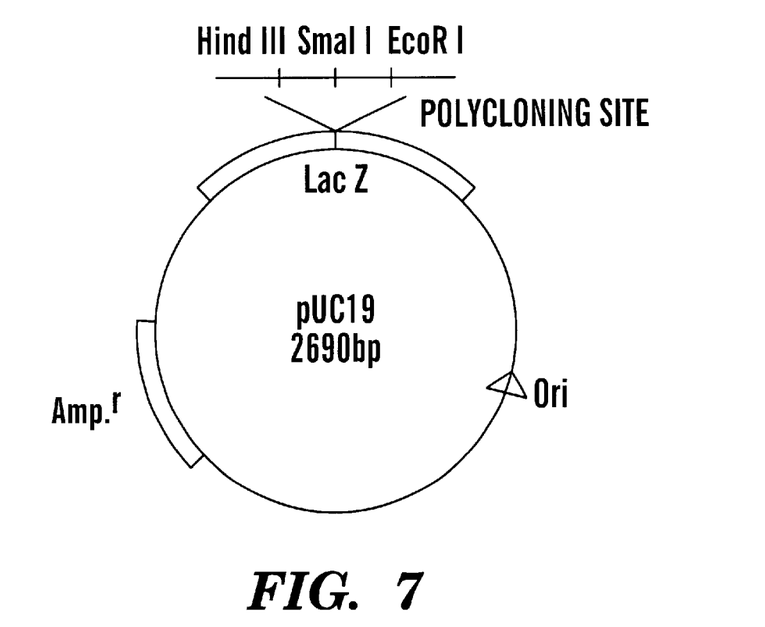
FIG. 7 is a construct map of plasmid pUC19.

FIGS. 6 and 7 present construct maps of plasmid pDO432 and plasmid pUC19.

Transformation by Introduction of Exogenous DNA into Ovaries via the Pollen Tube Pathway The present inventive method takes advantage of natural fertilization processes in transformation is the introduction of donor or exogenous DNA into ovaries at approximately the time of fertilization or right after fertilization. After pollination, pollen tube pathways form to allow the pollen tube(s) carrying two sperm nuclei to pass through the nucellus, and reach the egg apparatus to complete the double fertilization. The exogenous DNA goes along this pollen tube pathway into the embryonic sac, egg, and zygote (FIGS. 1 and 2). Generally, these cells do not have normal cell walls and could be considered as natural protoplasts to take up foreign DNA.

Several refined methods of ovary treatment have been reported, for example, microinjection procedures, including using isolated barley ovules, and Hepher et al. (1985) injected exogenous DNA into the ovary loculus of *Salpiglossis sinuata*. As an example, ovaries were injected with the plasmid pGV3850 between 15 and 18 hours after pollination. The seeds obtained were screened for the expression of the nopaline synthase gene. No transformants were reported.

Botany of Onion Flowers

The inflorescence of the onion is an umbel. It is an aggregate of many small flowers. Onion may have 100 to over 2000 flowers per umbel, largely depending on the bulb size, vigor, and the number of umbels produced by each bulb. Up to 20 flower stalks may be produced per bulb, but 3 to 6 are commonly seen. Each individual flower is made up of six stamens and one pistil (FIGS. 3, 4 and 5). The ovary contains three loculus, each of which contains two ovules. The anthers shed pollen over a period of three or four days prior to the time when the full length of the style is attained. The stigma becomes receptive at this time and as a result of delayed female maturity, cross-pollination is favored. The progress of flower opening on the umbels of *A. cepa* is somewhat irregular, though there is a tendency for flowers to open first in the most heavily isolated area of the umbel, usually that facing toward the sun at mid-afternoon or the warmest part of the day, and then to process roughly from the top of the umbel downwards. *A. fistulosum* has a completely regular pattern of flowering. In this species, flowering proceeds from the top of the umbel downward, so that a band of recently dehisced anthers occurs gradually down the umbel over a period of days, followed by a wave of receptive stigmas on long styles. If the plants produce two or more seed stalks, the flowering sequence may actually occur for over more seed stalks, the flowering sequence may actually occur for over a month.

Onion's ovary is trilocular with two anatropous, bi-tegmic, and crassinucellar ovules in each loculus. The embryo sac is spheroidal with one egg cell, two large synergids, two polar nuclei, and three antipodals. After pollination, the pollen tubes may grow the length of the style in 12–24 hours, depending upon temperature and plant variety. Fertilization is about 24 hours after pollination. In *A. cepa*, the endosperm starts to divide immediately following fertilization, but the zygote does not divide until 4 or 5 days following pollination. Nine days after pollination, the embryo is at globular stage. Embryos mature in 36 days after pollination. In *A. fistulosum*, four or five days after anthesis (DAA), the zygote is at metaphase; five to six DAA, the embryo develops into globular stage; eleven DAA, it becomes spheroid; twelve to thirteen growing points form at the lateral side in the form of a concavity; thirteen to fifteen DAA, it reaches the stick-shaped stage by growing in length. Subsequent development of the embryo results in its curvature and in the elongation of the cotyledon. The embryo matures 35 days after pollination.

Since onion is a monocotyledonous plant, transformation with Agrobacterium vector has been difficult. It has been observed that abnormal outgrowths are associated with infection of onion bulbs with *Agrobacterium tumefaciens*. Although no results of transformation are available in *A. fistulosum*, it is probably sufficiently close to make a similar deduction that *A. fistulosum* does not respond to infection by *Agrobacterium tumefaciens*. However, genetic transformation offers great potential to onion breeding because of the long generation time and strict quality standards. Therefore, based on the flowering characteristics of onion, development of genetic transformation techniques via pollen tube pathway provide a worthwhile approach to plant transformation.

MATERIALS AND METHODS

Plant Materials

Plant materials used in this study included *A. cepa* cvs. Yula and Dai Maru, and TTU breeding line DG133; *A.*

*fistulosum* cv. Heshiko. All were grown in the P2 level greenhouse (NIH, 1981) of the Department of Plant and Soil Science, Texas Tech University, Lubbock, Tex. Flowering plants were used as recipient plants for transformation.

Transformation Procedures

Foreign Marker Gene

Plasmid pDO432 was used as a vector (FIG. 6). This plasmid contains the cauliflower mosaic virus 35S promoter fused to the firefly (*Photinus pyralis*) luciferase coding sequence and a nopaline synthase terminator sequence. This gene construct has been expressed in transgenic tobacco plants and was suggested as a marker gene in transformation research.

Plasmid DNA Extraction

*E. coli* cells containing plasmid pDO432 were grown overnight at 37° C. in 50 ml liquid LB medium having 50 μg/l ampicillin with agitation (270 rpm). Cell suspensions were centrifuged at 5000 rpm at 4° C. for 10 min. The culture pellets were resuspended in 2 ml of freshly prepared lysis solution (50 Mm glucose, 10 Mm ethylenediaminetetraacetic acid (EDTA), 25 Mm Tris-Hcl Ph 8, 2 mg/l fresh lysozyme), and incubated on ice for 40 min. Two milliliters of 0.2 M NaOH, and 1% sodium dodecylsulfate (SDS) was added to the cell suspension to digest cell walls and to denature proteins. The cell suspension was incubated on ice box for 20 min. Then 2 ml 5 M potassium acetate (KOAc) was added and the solution was incubated on ice for 20 min. The suspension was centrifuged at 10,000 rpm for 12 min. The supernatant was filtered through one layer of miracloth. One volume of cold isopropanol was added to the supernatant. The mixed solution was put in −20° C. freezer overnight and then was centrifuged at 10,000 rpm for 10 min. The pellet was resuspended in 500 μl of sterile double distilled water. The suspension was extracted 2 times with equal volumes of phenol/chloroform/isopropanol (PCI, 12:12:1) and once with equal volumes of chloroform/isopropanol (Cl, 24:1). The purified solution was mixed with 0.5 volume of 7.5 M ammonium acetate ($NH_4OAc$) and 2 volumes of cold ethanol, put in a −20° C. freezer overnight, and then centrifuged at 10,000 rpm for 10 min. The pellet was resuspended in 0.3 ml TE buffer (10 Mm Tris-Hcl Ph 8.0, 0.1 M NaCl, 1 Mm EDTA). The plasmid DNA was used either immediately or stored at 4° C.

Preparation of Plasmid DNA for Transformation

Plasmid DNA (pDO432) solution was prepared with 4 methods (Table 1). These four preparations without plasmid DNA were used as controls for this study.

Due to the different flowering times and availability of flowering plants in different cultivars, plasmid DNA solutions prepared with method 1 were used for transformation of DG133 and Heshiko plants, plasmid DNA solution prepared with methods 2, 3, and 4 were used for transformation of Yula, Dia Maru, and Heshiko, respectively.

Transformation Procedure

Transformation was conducted during onion flowering in a P2 level greenhouse (conforming to NIH guidelines, 1981). Pollen was harvested from mature dehisced anthers and was applied to fully receptive stigmas, i.e., when styles reached their final length of 4 to 7 mm and stigmatic knobs were fully developed and covered with secretion (FIG. 3). The styles were carefully severed with a sterile surgical blade at the top of the ovaries at 18 or 24 hours after pollination (FIG. 4). Then 5 to 6 μl of freshly prepared DNA solution or control solution was micropipetted immediately to the wounded area of decapitated styles (FIG. 5).

TABLE 1

Four plasmid DNA (pDO432) solution used to treat onion florets:

| Solution | Components | Final DNA Concentration |
|---|---|---|
| 1 | ½ strength MS liquid medium[1]<br>4 mg/l naphthalene acetic acid (NAA)<br>4 mg/l gibberellic acid ($GA_3$) | 4 mg/ml |
| 2 | ½ strength MS liquid medium<br>4 mg/l NAA, 4 mg/l $GA_3$<br>6.5% polyethylene glycol (PEG) | 4 mg/ml |
| 3 | ½ strength MS liquid medium<br>4 mg/l NAA, 4 mg/l $GA_3$<br>0.25% dimethyl sulfoxide (DMSO) | 4 mg/ml |
| 4 | ½ strength MS liquid medium<br>4 mg/l NAA, 4 mg/l $GA_3$<br>2.5 units/μl Hind III[2] | 4 mg/ml |

[1]MS medium (Murashige & Skoog, 1962.)
[2]Hind III cuts the plasmid molecule into linear form.

A completely random factorial design was used to treat DG133 flowering plants to test the effect of various DNA treatments on the fruit set (Table 2). Styles were severed at about 18 or 24 hours after pollination with mature pollen.

Decapitated florets were treated with plasmid DNA solution 1, or the same solution but without plasmid DNA (control solution), and without applying any DNA preparation or control solution to the decapitated florets. Each treatment was replicated three times. Each replication consisted of 7 umbels with about 20 florets in each umbel. Other unmatured florets in the same umbel were removed due to nonsychronous flowering. After 40 to 45 days, the number of florets with black seeds was counted to determine percent of fruit set, i.e., a fruit containing one or more full black seeds. Percentage data were arcsine transformed prior to statistical analysis.

TABLE 2

A completely random design with two factors to test the effects of various DNA treatments on the seed production of DG133:

| Application Time[1] | | | | | |
|---|---|---|---|---|---|
| 18 hours after pollination | | | 24 hours after pollination | | |
| Solution Type[2] | | | | | |
| Plasmid DNA | Control Solution | No Application | Plasmid DNA | Control Solution | No Application |
| Treatments | | | | | |
| 1 | 2 | 3 | 4 | 5 | 6 |
| 18 hrs + Plasmid DNA solution | 18 hrs + control solution | 18 hrs + no application | 24 hrs + Plasmid DNA solution | 24 hrs + control solution | 24 hrs + no application |

[1]Styles were severed at 18 or 24 hours following pollination, and 5–6 μl solution was immediately micropipetted onto the decapitated florets.
[2]Plasmid DNA solution consisted of 4 mg/ml DNA of pDO432, ½ liquid MS medium supplied with 4 mg/l NAA and 4 mg/l $GA_3$; Control Solution was the same as plasmid DNA solution but without DNA;
No solution was applied in no application treatment.

Yula, Dia Maru, and Heshiko were treated at 18 hours after pollination with these plasmid DNA preparations (Table 1). Mature seeds from DNA-treated and control florets were harvested.

Tracing Plasmid DNA in Ovules

After styles of DG133 were removed, 5–6 μl of ethidium bromide (EB) mixed with each of the 4 preparations of plasmid DNA (4 mg/ml) or control solution (see Table 2) was micropipetted onto the decapitated styles. Ovaries were collected at 24 hours after application of EB. Ovaries were rinsed three times with double distilled water, then three times with 50% ethanol. Ovaries were longitudinally sectioned by hand using a razor blade. Ovary sections were observed and photographed (Kodak Ektar 1000) with ultraviolet (UV) light ($\lambda$=405 nm) on an Olympus BH2 microscope with a reflected light fluorescence attachment and PM-10ADS automatic photomicrographic system. Plasmid DNA bound to EB had a pink color under UV light. A completely random design was used to test the efficiency of plasmid DNA solutions prepared with each of the 4 methods to enter ovules via the pollen tube pathway. Each plasmid DNA solution was used as a treatment. Each treatment was replicated three times with 50 ovules in each replication. In each replication, 50 ovules were observed. Number of ovules with a fluorescence signal under UV light was expressed as percentages of number of ovules with fluorescence signal/total ovules observed in each replication. Percentage data were arcsine transformed before statistical analysis.

the populations derived from seeds harvested from treated florets. Specific primers which flank the 282 bp portion from 1066 to 1347 in the firefly luciferase gene coding sequence were used for PCR amplification of target sequence fragments. Amplification was conducted in a total 50 $\mu$l reaction containing 2.5 units/$\mu$l Taq polymerase, 2 $\mu$M each of the 2 primers, 1×Taq polymerase 10×buffer, 2 Mm $MgCl_2$, 200 $\mu$M of mixed dNTP (all are products of Promega Inc., USA), 2–3 $\mu$g of template DNA, plus 10 $\mu$l of 2 Mm tetramethyl ammonium chloride to increase the specificity of amplification. The amplification reaction was run in a DNA Thermal Cycler (PERKIN ELMER CETUS, USA) for 25 cycles with 94° C. 1 min. for denaturing, 52° C. 1 min. for annealing, and 72° C. 2 min. for chain extension (manufacturer's use manual). PCR products were viewed with a UV illuminator on 1% agarose gel stained with EB.

| Primer | Sequence (5' to 3') | Size of Target DNA Fragment |
|---|---|---|
| 1 (20mer) | GGATATGGGCTCACTGAGAC (from 1066 to 1085) (SEQ. ID. No. 1) | |
| 2 (22mer) | GAAGTGTTCGTCTTGGTCCCAG (from 1326 to 1347) (SEQ. ID. No. 2) | 282bp |

Selection of Transgenic Plants
Sample Collection

Ovules from plasmid DNA treated and control florets were allowed to mature in situ in the greenhouse and harvested when the seed coat was black and hard. Seeds were planted in the P2 level greenhouse. Fresh leaves were collected after seedlings had 4–5 leaves. Approximately 4 g of leaf material from each plant was collected for analysis.
Genomic DNA Isolation Total genomic DNA was extracted using the method of Dellaporta et al. (1983). Leaves were ground in liquid nitrogen to fine powder and transferred into 50 ml centrifuge tubes. Prewarmed (65° C.) ten ml of extraction buffer (0.1M Tris-Hcl Ph 8.0, 0.05M EDTA, 0.5M NaCl and 1% hexadecyltrimethylammonium bromide (CTAB) and 2 ml 20% SDS were added. After mixing well, the centrifuge tubes were put into 65° C. water bath for 30 min., then 3 ml 5M KOAc was added to the tubes, and the tubes were incubated in ice bath for 30 min. The mixture was centrifuged at 12,000 rpm at 4° C. for 15 min. The supernatant was transferred to another tube through two layers of miracloth filter. Equal volume of cold isopropanol (−20° C.) was added to the supernatant. The tubes were put into −20° C. freezer for 1 hour or overnight for DNA precipitation. DNA pellets were isolated by centrifuging at 10,000 rpm for 10 min. The pellets were dissolved in 0.5 ml TE buffer, and then treated with RNAase (10 mg/ml) at 37° C. for 30 min. to digest RNAs. The DNA suspension was purified with PCl twice and Cl once. Afterwards, the DNA was precipitated again with equal volume of cold isopropanol in −20° C. freezer for 1 hour or overnight. Air-dried DNA pellets were resuspended in 200 $\mu$l TE buffer.
Polymerase Chain Reaction (PCR)

The PCR is an in vitro method for the enzymatic synthesis of specific DNA sequences, using two oligonucleotide primers that hybridize to opposite strands and flank the region of interest in the target DNA. This technique was used to screen PCR amplification primers derived from the firefly luciferase gene coding sequence.

```
5'GCTCGGTACCCGGATATGGGCTCCATGAGACTACATCAGCTATTC
            GGATATGGGCTCCATGAGACTACATCAGCTATTC
                   1066

TGATTACACCCGAGGGGGATGATAAACCGGGCGCGGTCGGTAAAGTT
TGATTACACCCGAGGGGGATGATAAACCGGGCGCGGTCGGTAAAGTT

GTTCCATTTTTTGAAGCGAAGGTTGTGGATCTGGATACCGGGAAAACG
GTTCCATTTTTTGAAGCGAAGGTTGTGGATCTGGATACCGGGAAAACG

CTGGGCGTTAATCAGTGAGGCGAATAATGTGTCAGAGGACCTATGATT
CTGGGCGTTAATCAGTGAGGCGAATAATGTGTCAGAGGACCTATGATT

ATGTCCGGTTATGTAAACAATCCGGAAGCGACCAACGCCTTGATTGACA
ATGTCCGGTTATGTAAACAATCCGGAAGCGACCAACGCCTTGATTGACA

AGGATGGATGGCTACATCATTCAGGAGACATAGCTTACTGGGACGAAG
AGGATGGATGGCTACATCATTCAGGAGACATAGCTTACTGGGACGAAG

ACGAACACTTCGGGGATCCTCTA-3'
ACGAACACTTC
          1346
```

Sequence analysis of clone D1-9-1. Top line is the sequence of the insert (large font letters) and pUC19 (small font letters) (SEQ. ID. No. 3); Bottom line is the sequence of part (282bp) of the luciferase gene coding sequence (SEQ. ID. No. 4); Primer sequences are bold.
Southern Hybridization PCR products in 1% agarose gel were blotted onto nitrocellulose membranes. The 282 bp fragments amplified from pDO432 plasmid DNA were used as probes by labeling with $\alpha$-[$^{32}$p]DCTP using a random priming procedure. The membranes were hybridized with the probes under high stringency conditions (2×SET containing 900 Mm NaCl, 120 Mm Tris-Hcl Ph 7.8, 10 Mm EDTA, 5X Denhardt's [0.1 g/l Ficoll, 0.1 g/l polyvinylpyrrolidone, 0.1 g/l bovine serum albumin], 0.5% SDS, 65° C., overnight). After hybridization, the membranes were washed with 1×SET (150 Mm NaCl, 20 Mm Tris-HCl pH 7.8, 1 mM EDTA, 0.1% SDS) twice at 65° C. for 1 hour, and exposed to autoradiography film (Hyperfilm-MP, Amersham International PLC).

Genomic DNA from PCR positive plants showing a 282 bp PCR fragment was digested with Bam Hl, electrophoresed on 1.5% agarose gels, and blotted onto nitrocellulose membranes. Membranes were hybridized with the 1.9 kb Bam HI fragment from plasmid pDO432 labeled with $\alpha$-[$^{32}$p]dCTP by the method as above. Hybridization and washing conditions were the same as above.

Cloning of 282 bp PCR Fragment

The 282 bp PCR product amplified from two PCR positive plants, D1-9 and D1-10 (*A. cepa* cv. Dai Maru), were cloned into Small site of the plasmid vector pUC19 (FIG. 7) using the procedure of Sambrook et al. (1989). The fragments were separated on 1% agarose gel by electrophoresis, cut out of the gel, and cleaned with US Bioclean DNA purification kit according to the manufacturer's protocol (DNA 74000 USBioclean, United States Biochemicals). The purified DNA fragment was blunted by Klenow fragment treatment at room temperature for 60 min. and phosphorylated by $T_4$ polynucleotide kinase at 37° C. for 30 min. Then the fragment was ligated into Sma/l site of pUC19 by $T_4$ DNA ligase at 15° C. overnight. Recombinant clones were isolated by selection of white clones in plates with 5-bromo-4-chloro-3-indolyl-b-galactoside (X-gal) and β-isopropylthio-b-D-glactoside (IPTG). Plasmid DNA from these clones was digested with EcoR I and Hind III, electrophoresed on 1% agarose gel and blotted onto nitrocellulose membrane. The membranes were hybridized with the 282 bp probe from pDO432 using the procedure described earlier.

Sequence of 282 bp PCR Fragment

The 282 bp insertion in pUC19 was sequenced using a DNA Sequencing Kit (Sequenase Version 2.0, United States Biochemicals, USA) according to the manufacturer's protocol. Two 10 bp long flanking sequences of Smal I site of pUC19 were used as forward and reverse primers. $\alpha$-[$^{35}$S]-dATP was used to label samples. Samples were electrophoresed on 6% polyacrylamine gel. The dried gel was exposed to autoradiography film (Hyperfile-MP, Amersham International PLC) overnight.

Transformation of *E. coli* Cell with Onion Genomic DNA

Genomic DNA from Southern positive and control plants were used for transformation of *E. coli* cells. Twenty μg of genomic DNA was added to an *E. coli* cell suspension in microcentrifuge tubes. Cell suspensions were heat-shocked for ½ min at 42° C., and 1 ml liquid LB medium was added. After incubating at 37° C. in a water bath for 1 hour, 200 μl of the mixed culture was plated on solidified LB medium containing 50 μg/l Ampicillin.

Luciferase Assay For Gene Expression

Luminometry assay was used to detect expression of the firefly luciferase gene expression. Eight PCR positive plants of Heshiko H1-5, H1-10, H2-37-2, H2-37-4, H2-37-5, H2-37-6, H2-37-9 and H2-37-12 and control plants were used. Young leaf (about 10 cm long) discs (0.5 cm in diameter) and 50 mg fresh young roots were soaked in 200 μl assay buffer (250 Mm N-2-hydroxyethylpiperazine-N$^1$-2-ethanesulfonic acid [HEPES], 120 M MgCl2, 33 mg ATP, 30 μl bovine serum albumin [BSA], 180 μl DMSO, 10 Mm Luciferin) for 20 min. Then samples were read with a luminometer (Microplate Luminometer 1000, Dynatech Laboratory, Ind.).

Total RNA Isolation

The total RNA of 8 PCR positive Heshiko plants, H1-5, H1-10 (plants from seeds harvested from florets treated with plasmid pDO432 preparation containing ½ MS liquid medium supplied with 4 mg/l NAA and 4 mg/l GA$_3$ at 18 hour following pollination), H2-37-2, H2-37-4, H2-37-5, H2-37-6, H2-37-9 and H2-37-12 (progeny from PCR positive Heshiko plant harvested from florets treated with plasmid pDO432 preparation containing ½ MS liquid medium supplied with 4 mg/l NAA and 4 mg/l GA$_3$ at 18 hour following pollination) were extracted using the method of Chomczynski and Sacchi (1987). Two grams of fresh young leaves (about 10 cm long) were frozen in liquid $N_2$ and ground into fine powder which was transferred to polypropylene tubes, and 15 ml phenol, 3 ml Cl, 1 ml 3M NaOAc and 15 ml homogenization buffer (HB, 4M guanidium thiocyanate, 25 Mm sodium citrate, 0.5% sarcosyl) were added. After shaking vigorously by hand for 10 sec and placing on ice for 15 min, the suspension was homogenized with a polytron for 30 sec. The tube was centrifuged at 12,000 rpm for 20 min at 4° C. The aqueous phase was transferred to another tube. Phenol/chloroform/isopropanol extraction was repeated. After centrifuging, the aqueous phase was transferred to another tube, and an equal volume of cold isopropanol was added, and the solution was incubated at −20° C. freezer for 1 hour. The tube was centrifuged again as above, and the supernatant was discarded. An RNA pellet was dissolved in 5 ml HB solution; and an equal volume of isopropanol was added to repeat the precipitation. Then the RNA pellet was washed with cold 80% ethanol. It was then dried and resuspended in 5 ml DEPC (diethyl pyrocarbonate) treated water, equal volume of 4M LiCl was added, and the tube was kept at 0° C. for 4 hours. The tube was centrifuged as above, and the supernatant was poured off. The pellet was resuspended in 1 ml of DEPC-treated water. One hundred μl 3M NaOAc and 2 ml of ethanol were added to the suspension which was then incubated at −20° C. freezer for 1 hour. The tube was centrifuged as above, and the supernatant was poured off. The pellet was washed with 70% cold ethanol, dried and resuspended in 50 ml of DEPC-treated water. The suspension was transferred to an Eppendorf tube and cooled at −80° C. freezer for 5 min. Then, the tube was centrifuged in 10,000 rpm for 10 min, and the supernatant was transferred to fresh tube.

Northern Hybridization

RNA samples (10–20 μg) were loaded on 1% agarose gels. The gel was run at 80 volts with 1×MOPS buffer (0.02 M 3-[N-Morpholino]propane-sulfonic acid, 0.01 M NaOAc, 0.001 M EDTA). After electrophoresis, the gel was soaked in 75 Mm NaOH for 20 min, and washed in DEPC-treated water for 15 min. Then the gel was soaked in 20×SSPE for 45 min, and blotted onto nitrocellulose membranes overnight in 20×SSPE. Membranes were hybridized with the 1.9 kb Bam Hl fragment from pDO432 labeled with $\alpha$-[$^{32}$P] dCTP by the random priming method. Hybridization was conducted at 42° C. overnight in 50% formamide, then membranes were washed twice for 30 min in 1×SET twice. After that membranes were exposed to autoradiography file (Hyperfilm-MP, Amersham International PLC).

Fluorescence In situ Hybridization

Root tips were collected from control plant of Heshiko, PCR positive plants H1-5, H1-10, H2-37-2, H2-37-5, H2-37-6, H2-37-9 and H2-37-12. Root tips were pretreated with $\alpha$-1-bromonaphthalene for 5 hours at 4° C., and an in situ hybridization procedure established in our laboratory was followed (Ricroch et al., 1992). Chromosome slide preparations were air dried for one week and baked at 56° C.

overnight before hybridization. The 1892 bp Bam HI fragment of the luciferase gene coding sequence in plasmid pDO432 was isolated and used as a DNA probe by labeling the fragment with biotinylated 21-dUTP using a nick translation labeling kit (Clonetech, USA) according to manufacturer's instructions. Unincorporated nucleotides were separated by NICK Spin Columns (Pharmacia LKB Biotechnology). Each slide was treated with Rnase by adding 200 µl Rnase (100 µg/ml, Sigma Inc.) to the slide, covered with a cover glass (20×22 mm), and incubated at 37° C. for 1 hour in a humidity chamber. Then the cover glass was removed. The slides were rinsed with minimal agitation in 4 changes of 2×SSC (17.5 g/l sodium chloride/ 8/8 g/l sodium citrate) with 2 min in each wash, dehydrated in 70%, 80%, 100% ethanol at room temperature with 2 min in each, then air dried. Chromosome slides were denatured in 70% formamide (Sigma Inc.), 2×SSC at 71° C. for 2 min., and quickly dehydrated with 3 rinses in chilled 70%, 80% and 100% ethanol, and completely air dried. Hybridization solution consisted of 9 µl formamide, 3 µl 20×SSC, 10 µl ddH$_2$O, and 5 µl of probe (1 µg/µl DNA). The hybridization solution was heated at 70° C. water bath for 5 min and immediately put into ice bath. The slides were hybridized by adding 30 µl of the hybridization solution, covered with cover glass (22×55 mm), sealed with rubber cement, and incubated in a moist chamber at 37° C. for 12–16 hours. After hybridization, slides were removed from the incubator, and the rubber cement and cover glass were removed. The slides were then washed in 5 changes of 2×SSC with 2 min for each wash. The slides were placed in BT buffer (0.1 M sodium bicarbonate, 0.3 M NaCl, 0.05% Tween 20) at room temperature, and drained but not dried. Each slide was incubated for 5 min at room temperature in 75 µl 5% BSA/BT (0.05 g of bovine serum albumin [Sigma Inc.] in 1 ml of BT buffer). Aliquots of 75 µl BSA/BT/Avidin (0.1 ml of BSA/BT, 0.3% avidin [Vector laboratory, Inc.]) were added to each slide. Slides were incubated in a moist chamber at 37° C. for 45 min, rinsed in 4 changes of BT buffer with 2 min each at 40° C., then in room temperature BT buffer. Slides were drained but not dried. Aliquots of 75 µl 5% GS (0.1 ml goat serum [Vector Laboratory, Inc.] mixed with 1.9 ml BT buffer) were added to each slide. Slides were incubated at room temperature for 5 min, and 75 µl of avidinlantibody mixture (15 µl antibody [Vector Laboratory, Inc.] and 1 ml of 5% GS) was added to each slide. Slides were incubated at 37° C. for 45 min, and washed in 4 changes of BT buffer with 2 min each at 40° C., then in room temperature BT buffer. BT buffer was drained from slides, and 75 µl of BSA/BT was added to each slide. Slides were incubated at 37° C. for 5 min, and rinsed in 4 changes of BT buffer at 40° C., then in room temperature BT buffer and drained but not dried. One drop of an antifade mixture (antifade [see appendix], 0.01% 4,6-diamidino-2-phenylindole (DAPI) and 0.1% propidium iodide) was added to each slide. Slides were counterstained with propidium iodide and 4,6-diamidino-2-phenylindole. Visualization and photographs were taken with an Olympus BH2 microscope λ with a reflected light fluorescence attachment and PM-10ADS automatic photomicrographic system (Kodak Ektar 1000 film, UV light λ=435 nm).

Selection of Transgenic Plants in the Progeny Populations from PCR Positive Plants In the spring of 1993, 10 of the PCR positive plants of Heshiko derived from the treatment of plasmid DNA+½ MS medium flowered. Because the plants were grown in the wells of plastic flats and did not develop well before entering the reproductive stage, each plant produced only one umbel, and each umbel only had a few florets which were much fewer than that of field-grown plants. Self-pollination would not produce seeds because anthesis occurs 3–4 days before stigmas become receptive, and open-pollination is favored in onion. In order to get seeds from these plants, they were put in one cage in the P2-level greenhouse, and uncontrolled sib pollinations were conducted. Seeds were harvested, and planted in the same greenhouse. When seedlings reached the 4–5 leaf stage, 4 g fresh leaves were collected. Previously described procedures were followed for genomic DNA extraction, PCR, Southern hybridization, and in situ hybridization.

For the Southern hybridization of genomic DNA from PCR positive plants in the second generation, genomic DNA was extracted using procedures provided by the Upjohn Company, Kalamazoo, Mich. 49001-0199, with a few amendments. Newly expanding leaf tissue (200–300 mg fresh weight) was placed into a whirl-pack bag. Grinding buffer (0.6 ml containing 100 Mm Sodium Acetate Ph 4.8, 50 Mm EDTA Ph 8.0, 500 Mm NaCl, 2% Polyvinylpyrrolidone, and 1.4% SDS) was added to the leaf sample. A one liter Corning bottle was rolled firmly across the surface of the bag repeatedly until the leaf tissue was disrupted and had the consistency of applesauce. The bag was cut at the corner, and all the sample was squeezed into a sterile 1.5 ml eppendorf tube and incubated at 65° C. for 10 minutes. Ten moles ammonium acetate was added and mixed thoroughly. The tube was centrifuged at room temperature for 10 minutes at 10,000 rpm, and then 0.6 ml volume of isopropanol was added and mixed well. The tube was chilled at −20° C. for 10 minutes. DNA was hooked or spooled with a capillary pipette and dissolved in sterile water. Appropriate amounts of 4 M NaCl were added to give a final concentration about 3.0 M to remove polysaccharides. The sample was precipitated with ethanol. The resulting DNA pellet was dissolved in TE buffer.

Transformation

Fruit Set Following Decapitation and Exogenous DNA Application

When the styles were removed 18 or 24 hours following pollination, more than 80% of florets treated yielded seeds regardless of the treatments applied. There were no significant differences in fruit set between foreign DNA application time, i.e., 18 and 24 hour after pollination, among DNA solutions, or interaction between application time and DNA solution (Table 2). The fruit set of florets treated with plasmid DNA solution (84.3%) or control solution without DNA (83.4%) were slightly higher than that of florets that were not treated with any solution (81.8%), although the difference was not significant. These phenomenon could be explained as the effect of plant growth regulator (NAA and GA$_3$) in plasmid DNA or control solution without DNA. NAA and GA$_3$ enhance development of fertilized ovules and increase fruit setting, and are used in plant in vitro ovule or ovary cultures of interspecific hybrids, and in onion ovule culture. So application of NAA and GA$_3$ to the decapitated onion florets may increase fruit set in this experiment. These results also suggested that most of the pollen tube has reached the ovules within 18 hours following pollination, which conformed to the previous reports that pollen tubes grew the entire length of the style within 12–24 hours.

TABLE 3

Effect of plasmid DNA solution and application time on fruit set (%)[1] after pollination and decapitation[2]

| Treatment | | Fruit |
|---|---|---|
| Time (hr) | Solution Type[3] | Set (%) |
| 18 | DNA | 85.3 |
| 18 | Control | 82.2 |
| 18 | No application | 80.6 |
| 24 | DNA | 83.3 |
| 24 | Control | 84.6 |
| 24 | No application | 83.0 |
| Significance[4] | | NS |
| Application time | | NS |
| Solution type | | NS |
| Time × Solution type | | NS |

[1]Data on fruit set percentages were arcsin transformed before statistical analysis; nontransformed data are presented.
[2]Styles were severed at 18 and 24 hours following pollination; 5–6 µl plasmid DNA or 20 control solution was micropipetted onto the decapitated florets immediately after severment.
[3]DNA solution was prepared with method 1, i.e., 4 mg/l plasmid DNA + ½liquid MS medium supplied with 4 mg/l NAA and 4 mg/l GA$_3$; control solution was the same as plasmid DNA solution except no plasmid DNA; solution was not applied to decapitated floret in the no application treatment.
[4]Significant effect at P = 0.05(*) or nonsignificant (NS).

Movement of Plasmid DNA into Ovules

Within 24 hours after the application of EB-labeled DNA solution to the decapitated styles, fluorescence signals were observed in the remaining part of the style and on the surface of ovule. Heavy, distinct staining was detected around the surface of ovule and within the nucellus tissue, respectively. Generally, fluorescence signals appeared around the ovules. However, not all ovules had fluorescence signals in their wall or inside ovules upon observation after the application of EB-labeled plasmid DNA. With application of EB labeled plasmid DNA prepared with each of the different four methods, the numbers of ovules with fluorescence signal were significantly different (Table 4). Among the 4 plasmid DNA preparation methods, the plasmid DNA prepared with method 4 (4 mg/l plasmid DNA +0.25% DMSO +½ liquid MS medium supplied with 4 mg/l NAA and 4mg/l GA$_3$) yielded the highest number of ovules showing fluorescence signal after application onto decapitated styles, followed by the plasmid DNA prepared with method 3 (4 mg/l plasmid DNA +6.5% PEG +½ liquid MS medium supplied with 5mg/l NAA and 4 mg/l GA$_3$). There are reports showing the DMSO can be used as a carrier solution and help the transportation of chemicals such as plant growth regulators, colchicine, and Lauricidin into cells. PEG has been used to mediate DNA transfection into plant protoplasts and subsequent genetic transformation. Recent research showed the exogenous DNA (expression vectors containing cauliflower mosaic virus 35S promoter and chloramphenicol acetyl transferase [CAT] gene) were delivered into maize microspores using PEG treatment. In maize, PEG is able to inhibit both pollen and stigma nuclease activities which could digest exogenous DNA. Therefore, plasmid DNA mixed with 0.25% DMSO or 6.5% PEG would be helpful to transport DNA molecules into ovules via pollen tube pathway. Hind III cuts the plasmid pDO432 into linear form. It was supposed that plasmid DNA solution containing Hind III would cut plasmid molecules into linear form and recognize the same restriction site in the host's genomic DNA when the solution reached to the embryo sac, which may help the exogenous DNA insertion into the host's genomic DNA. But the number of ovules with fluorescence signal treated with plasmid DNA containing Hind III was less than that treated with plasmid DNA containing 0.25% DMSO or 6.5% PEG. These results indicate that each of the 4 DNA preparations when dropped onto the surface of decapitated styles reached the ovules via pollen tube pathway within 24 hours following application.

TABLE 4

Percentage of ovules with fluorescense signal after application of EB labeled plasmid DNA[5]

| Solution[6] | Ovules with Signal (%)[7] |
|---|---|
| DNA with 0.25% DMSO | 41.4 ± 0.7 a |
| DNA with 6.5% PEG | 38.4 ± 1.1 b |
| DNA with Hind III | 37.2 ± 0.8 b |
| DNA | 37.1 ± 1.3 b |

[5]Data on percentages of ovules with fluorescence signal were arcsin transformed before 20 statistical analysis; nontransformed data are presented.
[6]All the plasmid DNA preparations contained ½ MS medium supplied with 4 mg/l NAA) and 4 mg/l GA$_3$.
[7]Significant effect at LSD$_{0.05}$ = 1.1.

Selection of Transgenic Plants

Six populations (Table 5) were generated from each of the four DNA treatments involved with 2 A. *cepa* cultivars, one breeding line (with 2 application times), and one A. *fistulosum* cultivar. Morphologically, all plants in these 6 populations were similar to their respective control plants. Using 2 specific primers (covering 282 bp) of the luciferase gene construct, genomic DNA from seedlings with 4–5 leaves, and PCR amplification, plants were found in all 6 population that contained the 282 bp band (Table 5). None of control plants had the 282 bp fragment. Application of plasmid DNA mixed with ½ liquid MS medium containing 4 mg/l NAA, 4 mg/l GA$_3$, and 0.25% DMSO onto decapitated styles of florets of Dai Maru had the highest frequency of PCR positive plants in the population, followed by application of plasmid DNA mixed with ½ liquid MS medium only containing 4 mg/l NAA and 4 mg/l GA$_3$. In the transformation of Dictyostelium discoideum, electroporating Bam HI or Eco RI together with 4–6 plasmids cut with the same enzyme stimulated the efficiency of transformation more than 20-fold over the rate seen when plasmid DNA alone was introduced. It was found that restriction enzyme-mediated integration could generate insertions into genomic restriction sites in an apparently random manner. In this experiment, however, plasmid DNA mixed with restriction enzyme Hind III, which cuts the plasmid into linear form did not yield a higher frequency of PCR positive plants when compared with other treatments at 18 hours following pollination. Probably, the activity of the restriction enzyme after mixing with ½ liquid MS medium and applied onto the surface of decapitated florets was not as high as in the in vitro system reported in the transformation of Dictyostelium discodeum by electroporation (Kuspa & Loomis, 1992). In DG 133, application of plasmid DNA at 18 hours after pollination produced more PCR positive plants (15.1%) than that at 24 hours following pollination (12.3%). This suggests that 24 hours following pollination could be slightly too late for plasmid DNA to enter ovules of A. *cepa* and have a chance to incorporate into the onion genome. The frequency of PCR positive plants was correlated with the number of ovules with fluorescence signal after application of plasmid DNA prepared with 4 different methods. These PCR amplified bands strongly hybridized to the probe of luciferase gene coding sequence prepared from its PCR product. As expected, no positive signal was identified in the control plants.

In order to validate whether the PCR amplified 282 bp fragment is a part of the luciferase gene coding sequence, the 282 bp PCR fragments amplified from the genomic DNA of Dia Maru plant D1-9 and D1-10 were cloned into the Sma I site of plasmid pUC19. Ten clones were picked by selection of white clones in plates with 5-bromo-4-chloro-3-indoly-b-galactoside (X-gal) and β-isopropylthio-b-D-glactoside (IPTG). Plasmid DNA from these clones was digested with EcoR I and Hind III and electrophoresed on 1% agarose gel. Four clones, D1-9-1 and D1-9-5 from plant D1-9, D1-10-4 and D1-10-5 from Plant D1-10 had the ca. 282 bp insert. Southern hybridization results indicated that the 282 fragment also showed that it was identical to the specific part of the luciferase coding sequence covered by the two primers used in the screening of transformed plants.
TGATTACACCCGAGGGGGATGATAAAC-CGGGCGCGGTCGGTAAAGTT TGATTACAC-CCGAGGGGGATGATAAACCGGGCGCG-GTCGGTAAAGTT
GTTCCATTTTTTGAAGCGAAGGTTGTG-GATCTGGATACCGGGAAAACG GTTC-CATTTTTTGAAGCGAAGGTTGTG-GATCTGGATACCGGGAAAACG
CTGGGCGTTAATCAGTGAGGCGAATAAT-GTGTCAGAGGACCTATGATT CTGGGCGTTAAT-CAGTGAGGCGAATAATGTGTCAGAGGAC-CTATGATT
ATGTCCGGTTATGTAAACAATCCG-GAAGCGACCAACGCCTTGATTGACA ATGTCCGGT-TATGTAAACAATCCGGAAGCGAC-CAACGCCTTGATTGACA
AGGATGGATGGCTACATCATTCAGGAGA-CATAGCTTACTGGGACGAAG AGGATGGATGGCTA-CATCATTCAGGAGACATAGCTTACTGGGACGAAG into the onion genome. *E. coli* cell suspensions were treated with either genomic DNA from Southern positive plants DG 133 and H1-5 or from control plants. However, no clones could be seen on the plates containing LB medium with 50 mg/l ampicillin after incubating the cell suspension for 24 hours at 37° C. This result, because no *E. coli* cell suspension treated with genomic DNA from control plants could be transformed, suggested that there were not any endogenous plasmid DNA in onion cells.

To provide further evidence that the luciferase gene coding sequence has been integrated into onion genomic DNA, root tips from 2 Southern positive Heshiko plants, H1-5 and H1-10, and control plants were analyzed by fluorescence in situ hybridization with the 1.9 kb luciferase gene coding sequence. Hybridization signals were observed as yellow-green spots on a background of orange stained nuclei or chromosomes. Among 15 root tips of plant H1-5, signals were detected on nuclei or chromosomes in the cells of 11 root tips. In another plant H1-10, cells of 9 out of 15 root tips showed hybridization signals. No hybridization signal was detected on nuclei or chromosomes in the root tip cells of control plants. However, fluorescence signals were not constantly observed in the same position within the same chromosome. Therefore, in this case, in situ hybridization could not confirm the incorporation of luciferase gene construct into onion genome.

Furthermore, expression of the luciferase gene construct was not detected in the young leaves or roots from PCR positive Heshiko plants H1-5 and H1-10 by luminometry. Also, Northern blotting of total RNAs from these plants did not yield the expected hybridization signal, which indicated that the luciferase gene coding sequence was not transcribed.

TABLE 5

Number of plants with the 282 bp fragment of luciferase gene construct in 6 populations of the first generation

| Variety | Solution[8] | Seeds Obtained | Established Seedlings | No. of Plants Screened | No. of Plants with 282 bp Fragments | Frequency (%) | No. of Maturing Plants with 282 bp Fragment |
|---|---|---|---|---|---|---|---|
| Dai Maru | DNA + 0.25% DMSO | 87 | 49 | 49 | 9 | 18.4 | not available[9] |
| Yula | DNA + 6.5% PEG | 89 | 53 | 53 | 8 | 15.1 | not available |
| Heshiko | DNA + Hind III | 109 | 83 | 83 | 12 | 14.5 | not available |
| DG 133 | DNA | 119 | 73 | 73 | 11 | 15.1 | 4 |
| DG 133 | DNA (24 hours) | 94 | 57 | 57 | 7 | 12.3 | not available |
| Heshiko | DNA | 106 | 84 | 84 | 13 | 15.5 | not available |

Genomic DNAs from the PCR positive DG 133 and Heshiko plants from the seeds derived from the florets treated with plasmid DNA containing 1/2 MS liquid medium supplied with 4 mg/l NAA and 4 mgl GA$_3$ at 18 hours following pollination
[8]All the DNA preparations contained 1/2 MS medium supplemented with 4 mg/l NAA and 4 mg/l GA$_3$; except DG133, all other treatments were application of DNA at 18 hours following pollination.
[9]These plants were dead before analysis.

were digested with Bam Hl, and hybridized with 1.9 kb probe prepared from the luciferase gene coding sequence. Not all the PCR positive plants were also positive in Southern blotting. Only 5 DG 133 and 3 Heshiko plants showed the 1.9 kb band. According to the Southern hybridization results, the transformation frequency in the population of DG 133 and Heshiko from the seeds derived from florets treated with plasmid DNA containing ½ MS liquid medium, 4 mg/l NAA, and 4 mg/l GA$_3$ were 5.4 and 3.6% respectively.

The genomic DNA from Southern hybridization positive and control plants were used to transform *E. coli* competent cells to test whether the plasmid DNA delivered via pollen tube-pathway was in free status or probably incorporated When the PCR positive plants of DG133 were bulbing, genomic DNA from young leaves were extracted for PCR analysis. Four PCR positive plants (DG1-50, DG1-45, DG1-33, DG1-38, and DG3-56) which were positive in genomic Southern analysis at the young growth (4–5 leaves) stage, still had the 282 bp fragment amplified by PCR at maturing state. These plants were allowed to bulb. When the young leaves emerged from the bulbs, genomic DNA was extracted and PCR analysis was conducted. Among these 5 plants, only one kept the 282 bp fragment. It seemed that the luciferase gene construct disappeared during the plant development and differentiation in these 4 putative transgenic plants. These plants died in the greenhouse.

Selection of Transgenic Plants in the Progeny from PCR Positive Plants

Through self and sib pollination, 9 progenies were generated from 9 PCR positive Heshiko plants from seeds derived from florets treated with plasmid pDO432 preparation containing ½ MS liquid medium supplied with 4 mg/l NAA and 4 mg/l GA$_3$ at 18 hours following pollination. PCR analysis of genomic DNA from young leaves of these progeny (5–6 leaves) indicated that some plants among 7 progeny populations still had the 282 bp fragment of luciferase gene coding sequence. In 3 progenies, the PCR positive plants maintained the 282 bp fragment at their maturing state, but 2 progeny

TABLE 6

Number of plants with the 282 bp fragment of luciferase gene construct in 9 progeny lines derived from PCR positive Heshiko plants[10]

| with Progeny | No. of Plants Analyzed | No. of Plants with 282 bp Fragment | Transmission Frequency % | No. of Plants 282 bp Fragment at Maturing State |
|---|---|---|---|---|
| H2-25 | 12 | 3 | 25.0 | not available[11] |
| H2-26 | 8 | 2 | 25.0 | not available |
| H2-33 | 9 | 3 | 33.3 | 3 |
| H2-35 | 8 | 0 | 0.0 | — |
| H2-36 | 20 | 17 | 85.5 | 17 |
| H2-37 | 11 | 6 | 54.5 | 6 |
| H2-40 | 18 | 0 | 0.0 | — |
| H2-41 | 20 | 6 | 30.0 | not available |
| H2-42 | 12 | 2 | 16.7 | not available |

[10]PCR positive plants from the seeds derived from florets treated with plasmid DNA + ½ MS medium supplied with 4 mg/l NAA and 4 mg/l GA$_3$.
[11]These plants were dead before analysis.

populations did have any PCR positive individuals. Moreover, genomic DNA from PCR positive plants in progeny H2-36 showed a weak 1.9 kb band after digestion with Bam Hi and hybridized with the 1.9 kb luciferase probe. Although these data could not be analyzed for Mendelian inheritance, as the progeny were not derived from self-pollination, there is the possibility that the luciferase gene coding sequence introduced into onion genome by the pollen tube pathway could be transmitted to progeny through sexual route. Young leaves and roots from 6 PCR positive plants in progeny population H2-37 were selected for the luciferase gene expression assay. As in the first generation, no expression of the luciferase gene construct was observed by luminometry. In addition, these plants were negative when analyzed by Northern hybridization, which indicated that no transcript product was produced.

Transformation Mechanism via the Pollen Tube Pathway

After pollination in flowering plants, the pollen tube elongates along the style tissue and forms a pathway. This allows the pollen tube(s) carrying two sperm nuclei to pass down the style and into the ovary where it reaches the micropyle of an ovule and penetrates it. The pollen tube grows toward some of the synergids of the embryo sac where it bursts and discharges its cytoplasm and the two sperm cells into the usually degenerated or degenerating synergid. One of the sperm cell fuses with the two polar nuclei to form the triploid endosperm. A coordinated development of embryo, endosperm, and sporophytic tissues of the ovule and ovary then leads to the formation of seeds and fruits. The assumption of genetic transformation via the pollen tube pathway is that the exogenous DNA goes along this pollen tube pathway into the embryonic sac and then into the egg, zygote or early embryonic cells, dependent upon the time of entrance. According to embryological studies in angiosperms, the transformation from the egg to the zygote involves the secretion of a Periodic acid-Schiff (PAS)-positive wall over the cell boundary. The unfertilized eggs of most species have a cell wall confined to their basal (micropylar) portion, while the apical (chalazal) portion is bounded only by the plasmalemma. Therefore, egg cells or zygotes could be considered as natural protoplasts to take up foreign DNA. The mechanism involved in the integration of exogenous DNA into host's embryonic genome via the pollen tube pathway could be one of the following: (1) exogenous DNA reaches the egg cell along with two sperm cells and incorporates into the host genome during the fusion of the egg cell and sperm; and (2) exogenous DNA enters the embryo sac after fertilization and uptake by the zygote, the integrates into the host genome during the S-phase of the zygote at mitosis. Although data on cell walls of egg cells and zygotes of onion are not available, fertilization occurs 24 hours after pollination, and the zygote of *Allium cepa* does not start the first cell division until 4–6 days following fertilization. But the zygote of *Allium fistulosum* is at metaphase at 2 days after pollination. In this study, observation of fluorescence signals in ovules using EB-labeled exogenous DNA indicated that the applied DNA actually reached the ovules with 24 hours through the unobstructed path provided by severed pollen tube in the remaining part of the excised style into ovules because of the flux of the grain contents basipetally towards the base of the style. The applied DNA could go down along the space between the pollen tube and the transmitting tissue toward the ovule. Other research also demonstrated that in cotton, $^3$H-labeled exogenous DNA could pass from the micropyle to the open nucellus by the pollen tube pathway. Once the applied DNA reaches the embryo sac, uptake of exogenous DNA by the egg cell, or zygote may be relatively easy since, in most angiosperms, these cells lack a complete cellulose wall. In this study, exogenous DNA mixed with DMSO may have facilitated the DNA molecules reaching the ovules via the pollen tube pathway due to the penetration property of DMSO to plant tissue. Addition of ½ MS liquid medium, NAA and GA$_3$ to the DNA increased fruit set which may indirectly increase the efficiency of transformation.

Application of PCR in Detecting Transgenic Plants

The polymerase chain reaction technique has revolutionized molecular genetics by making possible a whole new approach to the study and analysis of genes. In this experiment, the PCR technique was used to screen for transgenic plants, and it proved to be very useful in the identification and analysis of transformed plant tissue based on the result of sequence analysis of the amplified product. The PCR technique has also been used for screening and identification of transgenic plants in other species. In general, this technique is flexible, requires DNA of moderate quality and is capable of specifically amplifying foreign genes from plant genomic DNA within a few hours. In agreement with other reports, oligonucleotide primers of about 21 bases in length is advisable. Of course, any contamination should be avoided to eliminate false positives.

Exogenous DNA Application Time Following Pollination

In *Allium cepa*, pollen tubes grow the entire length of the style within 12 to 24 hours after pollination. After fertilization, the endosperm nuclei soon divide and continue normally the first 5 days after pollination in *A. cepa*. However, the zygote does not divide until 4–6 days after pollination. Previous experiments in our laboratory showed that decapitation of styles before 6 hours after pollination failed to yield any seeds. In this study, application of plasmid DNA to the surface of decapitated florets 18 hour following pollination produced fruit set higher than 80%. Although there was no significant difference in fruit set between application of exogenous DNA 18 or 24 hours following pollination, PCR screening for putative transgenic plants indicated that plants with DNA application 18 hours following pollination had a higher frequency of PCR positive progeny than those 24 hours following pollination in DG133 (*A. cepa*). This was probably because some of the unobstructed paths provided by pollen tubes degenerated at 24 hours following pollination since the pollen tubes are unstable and have a relatively short life span. Thus plasmid DNA applied 24 hours following pollination may have had fewer pathways to enter the ovules. Therefore, based on the studies of onion pollen tube growth, foreign DNA should be applied to the decapitated onion florets no later than 18 hours following pollination to provide the applied exogenous DNA with a greater chance to enter ovules, and be taken by egg cells or by zygotes.

Based on the results of PCR screening of genomic DNA, the transformation frequency in onion was 12–15% in the plants from the seeds harvested from florets treated with each one of the 4 plasmid DNA preparation. Transformation frequency by the pollen tube-pathway in onion is a little higher than that obtained in cotton, lower than that in rice but much higher than that in barley. In these 3 species, total exogenous genomic DNA, plasmid p35S-NPTII and p35S-NPTII-Hist3, and PGSGLUC1 were used, respectively. These provide evidences that transformation frequency by the pollen tube pathway may differ by plant species according to their flower structure; the time and duration of the pollination and fertilization; and the source of exogenous DNA and the DNA construct.

Stability of Transformation via Pollen Tube Pathway

In order to obtain stable transgenic plants, the chimeric status of incorporated foreign gene must be avoided. In this experiment, although PCR analysis, Southern blotting, and non-transformation of *E. coli* cells by genomic DNA from 5 Southern positive plants (DG1-50, DG1-45, DG1-33, DG1-38, and DG3-56 at 4–5 leaves stage) showed that the introduced luciferase gene construct could be integrated into the onion genome, the 282 bp fragment of the luciferase gene construct could not be detected in some of the PCR positive plants when they were at maturing states or in young leaves emerged from bulbs, and fragment totally disappeared in progeny lines of *A. fistulosum* cv. Heshiko PCR positive plants H1-35 and H1-40. It appears that the introduced luciferase gene construct in some of PCR positive plants obtained in this study was incorporated in a chimeric or unstable fashion, and it did not constantly remain in the meristem tissue of the basal plate which generate young leaves or seed stalks during development and differentiation. Chimeric insertions of ex DNA can arise depending on the stage of development of the young embryo. DNA inserted intoan embryo with few cells would yield a plant with more cells containing the foreign DNA.

One of the crucial points for genetic transformation of plants is the expression of the introduced gene. Plasmid pDO432 contains the 35S promoter. However, no luciferase gene expression or transcript product was detected by luminometry in any of the putative transgenic onion plants tested. This is not beyond expectation since the luciferase gene construct contained the CaMV 35S promoter which has relatively low activity in monocot plants such as wheat. In barley, the kanamycin resistance gene with the 35S promoter which has relatively low activity in monocot plants such as wheat. In barley, the kanamycin resistance gene with the 35S promoter introduced by the pollen tube pathway only weakly expressed at the seedling level and lost its expression at maturity and after inheritance to the next generation. It seems that use of a strong promoter specific to monocot plant such as onion is very important in transformation investigations. Besides, cytidine methylation of DNA has also been implicated in the inactivation of inserted genes in transformed plant cells. Therefore, alterations by methylation of the promoter or the luciferase gene construct introduced are possible explanations for the non-expression of the luciferase gene construct in putative transgenic onion plants.

In terms of stable transformation, the foreign gene introduced into host plants has to be shown to pass through meiosis by demonstrating Mendelian segregation in the offspring of the primary transformant. In the experiment with Heshiko, 7 out of 9 PCR positive plants (from seed derived from florets treated with the plasmid pDO432 preparation containing ½ MS liquid medium supplied with 4 mg/l NAA and 4 mg/l $GA_3$ at 18 hours following pollination) still had the 282 bp fragment of the luciferase gene construct in their sexually produced progeny lines. Moreover, 3 available progeny populations maintained the 282 bp fragment in their maturing stages. Although these data could not be analyzed for Mendelian segregation due to uncontrolled sib pollination, this means that the introduced gene construct could have been integrated into Hesiko genomic DNA and contributed to cell lines developing into gametes. It was reported that the NPT-II gene introduced via the pollen tube-pathway, by PCR and Southern blotting, was in the self progeny of transgenic barley plants. Therefore, it is possible that the applied foreign DNA integrated into the chromosomes of egg cells, zygotes, or developing embryos (at the very beginning) via the pollen tube pathway in onion.

Since DNA transfer by pollen was considered a possibility to improve breeding by providing a means of transferring specific traits from one variety to another or from one species to another in the mid-seventies, many different transformation techniques using pollen as a vector or pollen tube-pathway such as the coculture of pollen with *Agrobacterium tumefaciens*, introduction of marker gene by microprojectile bombardment, and delivery of DNA into microspores by electroporation and PEG. However, these approaches to transformation via direct DNA uptake into pollen grains or sperm cells followed by normal pollination have not yet provided a reliable method of stable transformation. Although transformation of onion cells in bulb tissue by *Agrobacterium rhizogenes* has been reported, no feasible transformation techniques is currently available in onion. At present time, based on the results obtained, application of exogenous DNA prepared with proper methods to the removal wounding onion florets 18 hours following pollination has the potential to produce stably transformed plants.

What is claimed is:

1. A method for direct transformation of onion plants through the pollen tube pathway, comprising:
   pollinating the onion plant with mentor pollen thereby allowing formation of pollen tubes extending from the stigma down the styles into ovules;
   creating an ovary wound site by removal of styles from the ovary; and
   applying directly to the ovary wound site a solution of exogenous DNA,
   thereby introducing DNA comprising genes or gene constructs not present in the recipient onion plant genomes prior to transformation, thereby producing a transformed onion plant embryo.

2. A method according to claim 1 wherein the DNA comprising genes or gene constructs are introduced to the ovary wound site at about 18 to about 24 hours following pollination.

3. The method according to claim 1 wherein the DNA solution contains various concentrations of plant growth regulators NAA and $GA_3$.

4. The method according to claim 3 wherein the DNA solution further comprises DMSO.

5. The method according to claim 3 wherein the solution of DNA is comprised of plasmid DNA mixed with liquid ½ strength MS medium.

6. The method according to claim 4 wherein the solution of DNA is comprised of plasmid DNA mixed with liquid ½ strength MS medium containing 0.25% DMSO.

7. The method according to claim 1 wherein the ovary wound site is on an upper portion of the ovary and is substantially horizontal in relationship to the application of the solution of exogenous DNA from above.

8. The method according to claim 1 wherein the ovary wound site is created by surgical removal of the base of the styles.

9. The method according to claim 1 wherein the ovary wound site is creating by pulling the styles from the ovary.

10. The method according to claim 1 wherein the solution of exogenous DNA contains a segment of exogenous DNA which encodes a desired trait, and said DNA is introduced directly into the genome of the fertilized plant ovule so as to produce a transformed onion plant embryo, said method further comprising allowing said embryo to mature in situ.

11. The method according to claim 1 wherein the solution of exogenous DNA contains a segment of exogenous DNA which encodes a desired trait, and said DNA is introduced directly into the genome of the fertilized plant ovule so as to produce a transformed onion plant embryo, said method further comprising allowing said embryo to develop into a transformed onion plantlet on a growth medium, wherein the onion plantlet is capable of growth into a transformed onion plant.

12. The method according to claim 1 wherein the introduced solution is a solution of plasmid DNA comprising a DNA segment encoding a desired trait, introduced from about 18 to about 24 hours after fertilization to introduce the plasmid DNA into the genome of the fertilized onion plant ovule so as to produce a transformed onion plant embryo, said method further comprising cultivating said embryo on a growth medium to develop a transformed onion plantlet capable of growth into a transformed onion plant by allowing said embryo to mature in situ.

13. A method of transforming an onion plant comprising:
    providing a pre-pollinated onion plant with its floret styles removed to create an ovary wound site at which pollen tubes of the onion plant are exposed, and
    applying to the wound site a solution of DNA exogenous to the onion plant under conditions effective to transform the onion plant embryo with the DNA.

14. A method according to claim 13 further comprising:
    regenerating the transformed onion plant embryo under conditions effective to form a transformed onion plant.

15. A method according to claim 13, wherein said providing a pre-pollinated onion plant comprises:
    providing an onion plant having stigma connected by the style to an ovule;
    pollinating the onion plant with mentor pollen under conditions to permit formation of pollen tubes in the onion plant which extend from the stigma into the ovule; and
    removing the style from the onion plant to form the ovary wound site at which the pollen tubes of the onion plant are exposed.

16. A method according to claim 13, wherein the DNA solution further comprises at least one plant growth regulator.

17. A method according to claim 16, wherein the plant growth regulator is selected from the group consisting of NAA, $GA_3$, and combinations thereof.

18. A method according to claim 16, wherein the DNA solution further comprises DMSO.

19. A method according to claim 13, wherein the onion plant is a plant selected from the group consisting of *Allium cepa* L., *Allium fistulosum* L., *Allium satiuum* L., *Allium ampeloprasum* L., *Allium chinene*, *Allium schoenoprasum* L., *Allium galanthum*, *Allium royelii*, and *Allium tuberosum* L.

* * * * *